United States Patent
Kim et al.

(10) Patent No.: US 8,053,473 B2
(45) Date of Patent: Nov. 8, 2011

(54) ANTIBACTERIAL AGENT COMPRISING 7, 10-DIHYDROXY-8(E)-OCTADECENOIC ACID

(75) Inventors: Hak-Ryul Kim, Daegu (KR); Min Jung Suh, Daegu (KR)

(73) Assignee: Kyung Pook National University Industry-Academic Cooperation Foundation, Daegu (KR)

( * ) Notice: Subject to any disclaimer, the term of this patent is extended or adjusted under 35 U.S.C. 154(b) by 695 days.

(21) Appl. No.: 12/140,320

(22) Filed: Jun. 17, 2008

(65) Prior Publication Data

US 2009/0036533 A1  Feb. 5, 2009

(30) Foreign Application Priority Data

Aug. 1, 2007  (KR) .................. 10-2007-0077274

(51) Int. Cl.
*A61K 31/201* (2006.01)
*A61P 31/00* (2006.01)
*C12N 1/20* (2006.01)
*C12P 7/64* (2006.01)

(52) U.S. Cl. ............... 514/560; 435/134; 435/253.3

(58) Field of Classification Search .......... 514/560; 435/134, 253.3

See application file for complete search history.

(56) References Cited

U.S. PATENT DOCUMENTS 5,900,496 A * 5/1999 Hou .................. 554/124

OTHER PUBLICATIONS

CT Hou, et al., Growth Inhibition of Plant Pathogenic Fungi . . . , Journal of Industrial Microbiology & Biotechnology, vol. 24, pp. 275-276, 2000.
Seung Yong Shin, et al., Antibacterial Activity of Bioconverted Eicosapentaenoic . . . , International Journal of Food Microbiology, vol. 113, pp. 233-236, 2007.
Seung Young Shin, et al., Antibacterial Activity of Bioconverted . . . , Agric. Chem. Biotechnol., vol. 48, pp. 167-169, 2005.
Seung Yong Shin, et al., Antibacterial Activity of Various Hydroxy . . . , Agric. Chem. Biotechnol., vol. 47, pp. 205-205, 2004.
In-Ae Chang, et al., Production of 7, 10-Dihydroxy-8(E)-Octadecenoic . . . , Appl. Microbiol Biotechnol., vol. 74, pp. 301-306, 2007.

* cited by examiner

*Primary Examiner* — Herbert J Lilling
(74) *Attorney, Agent, or Firm* — Lucas & Mercanti, LLP

(57) ABSTRACT

The present invention relates to an antibacterial agent containing 7,10-dihydroxy-8(E)-octadecenoic acid (referred as DOD) as an active ingredient. DOD produced by the method of the present invention can be effectively used as an antibacterial agent because it has a wide spectrum of antibacterial activity against various microorganisms.

3 Claims, 8 Drawing Sheets

7,10-dihydroxy-8(E)-octadecenoic acid (DOD)

1  2  3  4

Fig. 7

Figure 1:
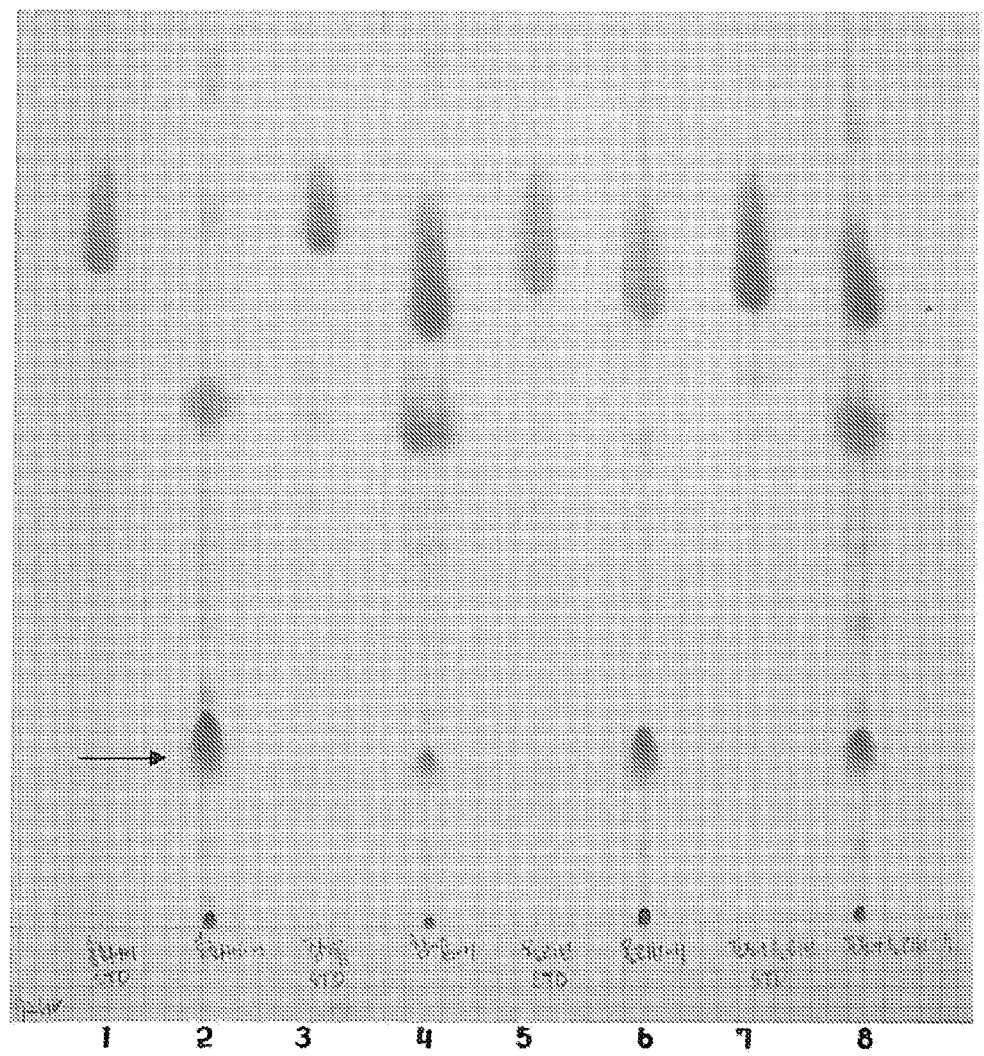

| Bacterial strains | Clear zone on plate (mm) [a] | | |
|---|---|---|---|
| | A | B | C |
| *Escherichia coli* ATCC 8739 (−) | 5 | −[b] | − |
| *Staphylococcus epidermidis* KCTC 1917 (+) | 3 | 1 | 1 |
| *Salmonella typhimurium* KCTC 2515 (−) | 8 | − | − |
| *Listeria monocytogenes* ATCC19111 (+) | 1.5 | − | 1 |
| *Staphylococcus aureus* ATCC 6538 (+) | 10 | − | − |
| *Bacillus subtilis* ATCC 6501 (+) | 3 | 1 | − | a) Distance from disk end, b) No inhibitory zone was formed.

A : DOD (1000 μg)  B : Oleic acid (1000 μg)  C : DMSO 15 μℓ

Fig. 8

| Microorganism | MIC (μg/mℓ) |
|---|---|
| Bacillus subtilis ATCC 6501 | <125 |
| Escherichia coli ATCC 8739 | 250 |
| Staphylococcus epidermidis KCTC 1917 | 250 |
| Salmonella typhimurium KCTC 2515 | 1000 |
| Listeria monocytogenes ATCC19111 | <125 |
| Staphylococcus aureus ATCC 6538 | 250 |
| Pseudomonas syringae pv. sesami KACC 10649 | 1000 |
| Pseudomonas syringae pv. actinidae KACC 10659 | 500 |
| Erwinia sp. KACC 10207 | <125 |
| Pseudomonas syringae pv. syringae KACC 10361 | <125 |
| Ralstonia solanacearum KACC 10475 | <125 |
| Corynebacterium glutamicum KACC 10784 | 1000 |
| Pseudomonas corrugata KACC 10141 | >8000 |
| Clavibacter michiganesis subsp. Michiganensis KACC 20122 | >8000 |

ANTIBACTERIAL AGENT COMPRISING 7, 10-DIHYDROXY-8(E)-OCTADECENOIC ACID

This application claims the benefit of Korean Patent Application No. 10-2007-0077274 filed Aug. 1, 2008 and the application document is incorporated herein in its entirety by reference.

TECHNICAL FIELD

The present invention relates to an antibacterial agent comprising 7,10-dihydroxy-8(E)-octadecenoic acid as an active ingredient.

BACKGROUND ART

Hydroxy fatty acid (HFA) is a compound where one or more hydroxyl groups are linked to the main chain of fatty acid. These hydroxyl groups endow specific characteristics including high viscosity or reactivity to fatty acid. According to the specific characteristics generated by the hydroxyl group, HFA exhibits various physiological functions so that it can be applied in the wide range of industrial fields including novel pesticides, novel medicines, high-functional resins and fibers, biodegradable plastic materials, lubricants, cosmetics, paints, etc. Ricinoleic acid, a derivative of castor oil, or sebacic acid has been used as a synthetic material for highly efficient polymer having new function so far, and this material is classified as 'industrially essential material' by US government. According to the number of hydroxyl groups linked to HFA, it is classified into mono-, di- and tri-hydroxy fatty acid and epoxy-hydroxy fatty acid or oxo-hydroxy fatty acid having an extra structure besides hydroxyl group are also included in this family.

Although many functions of hydroxy fatty acid have been known, only a minute amount of hydroxy fatty acids exists in plants in natural system. So, there have been attempts to produce hydroxy fatty acids using microorganisms. *Flavobacterium* sp DS5 has been reported to be able to produce 10-hydroxy-octadecadienoic acid from oleic acid, and such a production was presumably mediated by 10-specific hydratase. It was also reported that *Pseudomonas aeruginosa* PR3 could produce mono-, di- and tri-hydroxy fatty acid using wide range of substrates.

The present inventors completed this invention by identifying the compound produced by a microorganism using natural vegetable oil as a substrate to be 7,10-dihydroxy-8(E)-octadecenoic acid and further by confirming that this compound had antibacterial activity.

DISCLOSURE

Technical Problem

It is an object of the present invention to provide a method for preparing a culture solution containing 7,10-dihydroxy-8(E)-octadecenoic acid.

It is another object of the present invention to provide a culture solution containing 7,10-dihydroxy-8(E)-octadecenoic acid prepared by the above method of the present invention.

It is further an object of the present invention to provide a method for producing 7,10-dihydroxy-8(E)-octadecenoic acid from the above culture solution using an organic solvent.

It is also an object of the present invention to provide an antibacterial agent containing 7,10-dihydroxy-8(E)-octadecenoic acid as an active ingredient.

It is also an object of the present invention to provide a method to inhibit the growth of a pathogenic microorganism in food or environment using the above culture solution or 7,10-dihydroxy-8(E)-octadecenoic acid.

In addition, it is an object of the present invention to provide a method for treatment or prevention of infective diseases by a pathogenic microorganism in a subject using 7,10-dihydroxy-8(E)-octadecenoic acid.

Technical Solution

To achieve the above objects, the present invention provides a method for preparing a culture solution containing 7,10-dihydroxy-8(E)-octadecenoic acid (hereinafter referred as "DOD") having formula 1, comprising the following steps:

1) incubating *Pseudomonas aeruginosa* in a culture medium for 5-48 hours;

2) adding natural vegetable oil to the culture solution of step 1) by 0.01-10 weight %; and, 3) incubating the culture solution of step 2) additionally for 1-7 days and eliminating the cells:

<Formula 1>

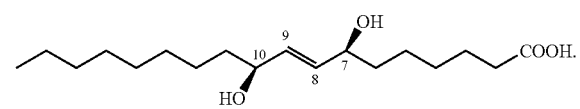

The present invention also provides a culture solution containing DOD prepared by the above method.

The present invention further provides a method for preparing DOD comprising the step of recovering DOD from the culture solution containing DOD by using an organic solvent.

The present invention also provides a method for inhibiting growth of pathogenic microorganisms in a food comprising the step of adding 7,10-dihydroxy-8(E)-octadecenoic acid to the food in an amount effective to inhibit the growth of the pathogenic microorganisms in soil or plants.

The present invention also provides a method for inhibiting growth of pathogenic microorganisms comprising the step of treating the culture solution or 7,10-dihydroxy-8(E)-octadecenoic acid to the soil or the plants in an amount effective to inhibit the growth of the pathogenic microorganisms.

The present invention also provides a method to treat or prevent on infective disease caused by a pathogenic microorganism in a subject comprising the step of administering 7,10-dihydroxy-8(E)-octadecenoic acid to the subject in an amount effective to inhibit the growth of the pathogenic microorganisms.

Hereinafter, the present invention is described in detail.

To achieve the above objects, the present invention provides a method for preparing a culture solution containing 7,10-dihydroxy-8(E)-octadecenoic acid having formula 1, comprising the following steps:

1) incubating *Pseudomonas aeruginosa* in a culture medium for 5-48 hours;

2) adding natural vegetable oil to the culture solution of step 1) by 0.01-10 weight %; and 3) incubating the culture solution of step 2) additionally for 1-7 days and eliminating the cells:

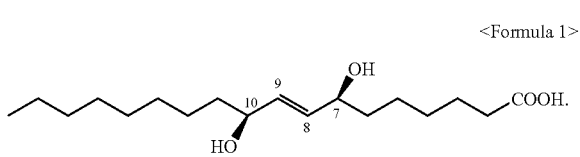

<Formula 1>

7,10-dihydroxy-8(E)-octadecenoic acid can be chemically synthesized or produced by a microorganism, but preferably produced by *Pseudomonas aeruginosa* using natural vegetable oil containing oleic acid, triolein or oleic acid as a substrate.

Figure 2:
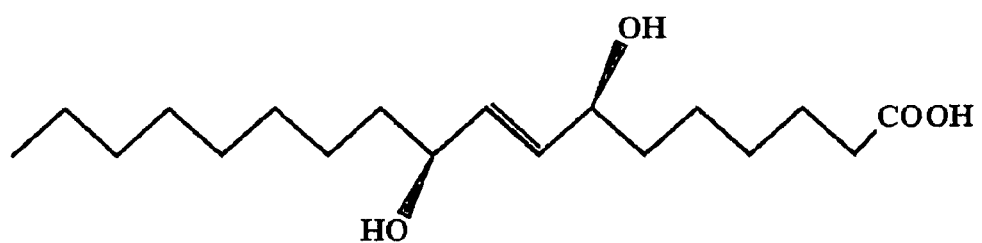
Figure 3:
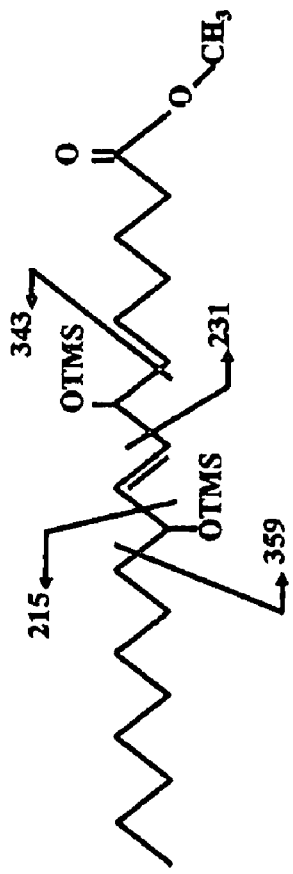
Figure 3:
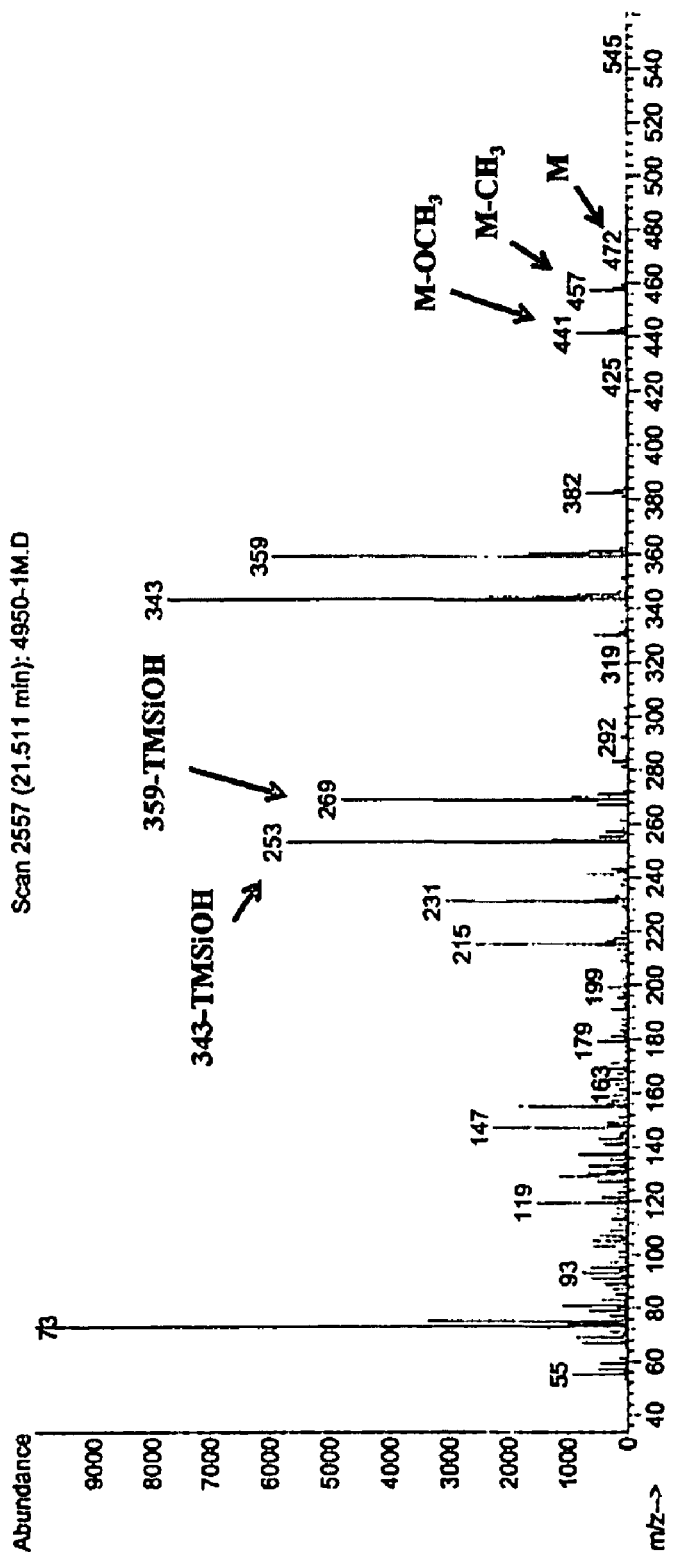

In a preferred embodiment of the present invention, *Pseudomonas aeruginosa* PR3 was cultured using safflower seed oil, sesame oil, olive oil or a mixture of olive oil and grape seed oil as a substrate. As a result, spots (arrows) distinguishing the culture extract from natural vegetable oil were detected (see FIG. 1) and a compound corresponding to the spot was collected (see FIG. 4). The compound was analyzed using gas chromatography/mass spectrometer, and as a result it was identified as DOD. DOD is a kind of hydroxy fatty acid, which contains two hydroxyl groups each linked to C7 and C10 of C18 fatty acid chain and a trans double bond between C8 and C9 (see FIGS. 2 and 3).

In step 1), the *Pseudomonas aeruginosa* strain is preferably *Pseudomonas aeruginosa* PR3. The strain was deposited at Agricultural Research Service Culture Collection, USA (NRRL B-18602).

In step 1), the culture time of *Pseudomonas aeruginosa* is preferably 5-48 hours and more preferably 24 hours. The culture temperature is preferably 10-45° C. and more preferably 28° C. The pH of the medium is preferably 4.0-10.0 and more preferably 7.0. The medium is preferably YPD medium (1% yeast extract, 2% peptone and 2% dextrose) and this medium may include glucose, fructose, sucrose, glycerol, xylose, galactose, maltose or lactose as a carbon source independently or as a mixture, instead of dextrose, and can contain malt extract, glutamine, ammonium nitrate, peptone, tryptone, ammonium chloride, ammonium sulfate, ammonium phosphate or urea as a nitrogen source independently or as a mixture, instead of yeast extract.

In step 2), the natural vegetable oil may be any one of oleic acid, triolein or any natural vegetable oil containing oleic acid, but preferably selected from the group consisting of olive oil, safflower seed oil, soybean oil, corn oil, sesame seed oil, perilla seed oil, grape seed oil, red pepper seed oil, canola oil, sun flower seed oil, melon seed oil, bran oil, hazelnut oil, triolein and a mixture thereof, but not always limited thereto. The natural vegetable oil may be prepared by any conventional method including solvent extraction or pressed extraction which has been most commonly used for extracting oil from seeds or fruits of a plant. And it is also possible to purchase the oil on the market. The natural vegetable oil is added to the culture solution by 0.01-10 weight % and more preferably by 1 weight %.

In step 3), the culture period is 1-7 days and more preferably 3 days.

The present invention further provides a culture solution containing DOD prepared by the above method.

The culture solution of the present invention characteristically has antibacterial activity against almost all the bacteria including Gram positive and Gram negative bacteria. In a preferred embodiment of the present invention, the antibacterial activity of the crude extract of the culture solution against various microorganisms was investigated by using a solid agar medium or a liquid medium. As a result, high antibacterial activity was observed at the concentration of 3 mg/spot (see FIG. 5). 7,10-dihydroxy-8(E)-octadecenoic acid separated from the culture solution exhibited high antibacterial activity against various microorganisms including Gram positive and Gram negative bacteria, so that it did not exhibit Gram dependent specific characteristics (see FIG. 7 and FIG. 8). Therefore, the antibacterial activity of DOD included in the culture solution against various microorganisms was confirmed. So, DOD can be effectively used for the prevention or treatment of infective diseases in human, animals and plants caused by various microorganisms or for the prevention of food decomposition.

The present invention also provides a method for producing 7,10-dihydroxy-8(E)-octadecenoic acid comprising following steps:
1) adding an organic solvent to above culture solution and then shaking them;
2) recovering an upper layer solution after two layers are separated; and,
3) removing the organic solvent from the upper layer solution.

The organic solvent herein can be ethyl acetate, diethyl ether, butanol, N-hexane or a mixture thereof, but not always limited thereto. In a preferred embodiment of the present invention, equal amounts of ethyl acetate and diethyl ether to the culture solution were used for extraction over two times stepwise. The extract was concentrated by rotary evaporator.

The producing method above can include the step of purification of 7,10-dihydroxy-8(E)-octadecenoic acid from the recovered upper layer using additional chromatography. The purification can be performed by crystallization taking advantage of difference of melting points, fractional distillation or column chromatography, in addition to the above chromatography, but not always limited thereto. In a preferred embodiment of the present invention, thin layer chromatography was performed for the purification (see FIG. 1).

The present invention also provides an antibacterial agent containing 7,10-dihydroxy-8(E)-octadecenoic acid as an active ingredient.

The antibacterial agent of the present invention characteristically has wide antibacterial activity against almost all Gram positive and Gram negative bacteria. In a preferred embodiment of the invention, the wide antibacterial activity of the above agent against various microorganisms was investigated using a solid agar medium or a liquid medium. As a result, high antibacterial activity was detected at the concentration of 5 mg/spot, which is the similar antibacterial activity level with that of the antibacterial ointment Bactroban, containing Mupirocin as an active ingredient, which is now sold in markets (see FIG. 5). The agent exhibited high antibacterial activity against various microorganisms including both Gram positive and Gram negative bacteria, so that no specificity acceding to Gram staining is observed (see FIG. 7 and FIG. 8). So, the antibacterial activity of DOD included as an active ingredient in the antibacterial agent of the present invention was confirmed, so that it is expected to be effectively used as a novel industrial antibacterial agent. DOD of the present invention has wide antibacterial activity against various microorganisms, so that it can also be effectively used for the treatment or prevention of infective diseases in human, animals and plants caused by pathogenic microorganisms and for the prevention of food decomposition.

The content of DOD, which is an active ingredient of the antibacterial agent of the present invention, can be adjusted according to the formulation method and the purpose of use, and can be determined as 0.0001-2000 mg/kg of a subject.

The antibacterial agent of the present invention can be formulated for oral administration, for example powders, granules, tablets, capsules, soft capsules, suspensions, emulsions, syrups and aerosols, and for parenteral administration, for example external use, suppositories and sterile injections, etc. The solid formulations for oral administration are prepared by mixing one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, solution, water-insoluble excipients, suspensions, emulsions, lyophilized preparations and. Suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

Parenteral administration is performed by systemic administration or local administration, and systemic administration is more preferred. Particularly, the parenteral administration is exemplified by transdermal injection, intramuscular injection, intravenous injection or rectal administration. For such parenteral administration, a syringe or drip or suppository is used or a preparation for parenteral administration is applied on the skin as an ointment, etc.

The effective amount of the antibacterial agent of the present invention can be determined according to weight and condition of a patient, severity of a disease, preparation of a drug, administration pathway and period. The effective amount of the antibacterial agent is preferably 0.0001-1000 mg/kg per day, and more preferably 100-200 mg/kg per day. The administration frequency can be once a day or a few times a day. The above amount and administration method cannot limit the scope of the invention in any way.

To prevent decomposition of food, food can be dipped in immersion solution containing the antibacterial agent of the present invention or the immersion solution can be sprayed on food. This agent can be added to food alone or together with other food ingredients. It can also be applied in every kinds of general food according to the conventional method. When food is dipped in the immersion solution, the content of the antibacterial agent and the immersion time are determined not to be too low to be effective and not to be too high to affect the food. In general, the content of the antibacterial agent in food or beverages is up to 15 weight % for the whole raw material and preferably up to 10 weight %.

The antibacterial agent of the present invention can be treated to seed of a plant or to the plant itself for sterilization and prevention of plant pathogens. If necessary, it is treated thereto by spraying or soaking. When it is sprayed, it can be either sprayed alone as it is or sprayed with other formulations together. It can be applied in every general plant according to the conventional method. For spraying, the agent can be formulated as liquid preparation, suspension, emulsion, and freeze-dried preparation, and then one of these formulations can be diluted in aqueous solution. When a seed of a plant is dipped in the liquid containing the agent, the content of the antibacterial agent and the immersion time are determined not to be too low to be effective and not to be too high to affect the seed.

The present invention also provides a method for inhibiting growth of pathogenic microorganisms in a food comprising the step of adding 7,10-dihydroxy-8(E)-octadecenoic acid to the food in an amount effective to inhibit the growth of the pathogenic microorganisms in soil or plants.

To prevent decomposition of food, food can be dipped in immersion solution containing DOD or the immersion solution can be sprayed on food. It can be used independently as it is or used together with other food ingredients. It can also be applied in every kinds of general food according to the conventional method. When food is dipped in the immersion solution, the content of DOD and the immersion time are determined not to be too low to be effective and not to be too high to affect the food. In general, the DOD content in food or beverages is up to 15 weight part for the whole raw material and preferably up to 10 weight part.

In a preferred embodiment of the present invention, DOD was treated to various microorganisms at different concentrations and the antibacterial activity thereof was investigated. As a result, microorganisms were not growing at a certain DOD concentration, suggesting that DOD inhibited the growth of microorganisms in liquid medium with demonstrating its antibacterial activity (see FIG. 6). Based on the results of the above experiment, the minimum concentration of DOD effective in inhibiting the growth of pathogenic microorganisms was determined (see FIG. 7 and FIG. 8).

The pathogenic microorganism can be selected from the group consisting of *Staphylococcus aureus, Bacillus subtillis, Escherichia coli, Staphylococcus epidermidis, Salmonella typhimurium, Listeria monocytogenes, Pseudomonas syringae* pv. *sesami, Pseudomonas syringae* pv. *actinidae, Erwinia* sp., *Pseudomonas syringae* pv. *syringae, Ralstonia solanacearum, Geotricum candidum, Rhizoctonia solani, Botrytis cinerea, Colletotrichum capsici, Fusarium oxysporum, Phytophtora capsici, Enterobacter agglomerans, Serratia marcescens, Yersinia pseudotuberculosis, Klebsiella pneumoniae, Arcanobacterium haemolyticum, Enterobacter intermedius, Agrobcaterium tumefaciens, Clavibacter michiganenesis, Erwinia chrysanthemi, Erwinia carotovora, Erwinia aroideae, Pseudomonas corrupta, Pseudomonas solanasearum, Pseudomonas gladioli, Xanthomonas campestris* pv. *citri, Xanthomonas campestri* pv. *prani, Botryosphaeria dothidea, Colletoricum gloesporiodes, Colletoricum acutuatum, Acidovora anthurii* sp. *Nov Agrobacterium* sp., *Malassezia furfur, Propionibacterium acnes, Trichophyton mentagrophytes, Trichophyton rubrum, Epidermophyton floccosum, Pseodumonas corrugate, Xanthomonas axonopodis* pv. *citri, Xanthomonas campestris, Cryptococcus neoformans, Candida albicans, Candida glabrata, Candida tropicalis, Rhodotorula rubra, Saccharomyces cerevisiae, Trichosporon beigelil, Pichia memebranefaciens* and *Corynebacterium glutamicum*, but not always limited thereto and any Gram positive or Gram negative microorganism can be selected.

The present invention provides a method for inhibiting growth of pathogenic microorganisms containing the step of treating the culture solution or 7,10-dihydroxy-8(E)-octadecenoic acid to soil or plants in an amount effective to inhibit the growth of microorganisms.

The culture solution or DOD of the present invention can be treated to seed of a plant or the plant itself for sterilization and prevention of plant pathogens. If necessary, it is treated thereto by spraying or soaking. When it is sprayed, it can be either sprayed alone as it is or sprayed with other formulations together. It can be applied in every general plant according to the conventional method. For spraying, the agent can be formulated as liquid preparation, suspension, emulsion, and freeze-dried preparation, and then one of these formulations can be diluted in aqueous solution. When a seed of a plant is dipped in the liquid containing the agent DOD, the concentration of DOD and the immersion time are preferably determined not to be too low and not to affect the seed.

The amount can be changed according to the kind of pathogenic microorganism, so it is not fixed. But, the preferable amount is 0.001 mg-50,000 mg/$m^2$ of the surface area of a plant.

The present invention also provides a method for treating or preventing infective diseases caused by a pathogenic microorganism in a subject comprising the step of administering 7,10-dihydroxy-8(E)-octadecenoic acid to the subject in an amount effective to inhibit the growth of the pathogenic microorganism.

The amount can be changed according to the kind of pathogenic microorganism, so it is not fixed. But, the preferable amount is 0.0001 mg-50,000 mg/kg.

The pathogenic microorganism can be selected from the group consisting of *Staphylococcus aureus, Bacillus subtillis, Escherichia coli, Staphylococcus epidermidis, Salmonella typhimurium, Listeria monocytogenes, Pseudomonas syringae* pv. *sesami, Pseudomonas syringae* pv. *actinidae, Erwinia* sp., *Pseudomonas syringae* pv. *syringae, Ralstonia solanacearum, Geotricum candidum, Rhizoctonia solani, Botrytis cinerea, Collectotrichum capsici, Fusarium oxysporum, Phytophtora capsici, Enterobacter agglomerans, Serratia marcescens, Yersinia pseudotuberculosis, Klebsiella pneumoniae, Arcanobacterium haemolyticum, Enterobacter intermedius, Agrobcaterium tumefaciens, Clavibacter michiganenesis, Erwinia chrysanthemi, Erwinia carotovora, Erwinia aroideae, Pseudomonas corrupta, Pseudomonas solanasearum, Pseudomonas gladioli, Xanthomonas campestris* pv. *citri, Xanthomonas campestri* pv. *prani, Botryosphaeria dothidea, Colletoricum gloesporiodes, Colletoricum acutuatum, Acidovora anthurii* sp. *Nov Agrobacterium* sp., *Malassezia furfur, Propionibacterium acnes, Trichophyton mentagrophytes, Trichophyton rubrum, Epidermophyton floccosum, Pseodumonas corrugate, Xanthomonas axonopodis* pv. *citri, Xanthomonas campestris, Cryptococcus neoformans, Candida albicans, Candida glabrata, Candida tropicalis, Rhodotorula rubra, Saccharomyces cerevisiae, Trichosporon beigelii, Pichia memebranefaciens* and *Corynebacterium glutamicum*, but not always limited thereto and any Gram positive or Gram negative microorganism can be selected.

The subject that can be applied by the method of the present invention is an animal or a plant, and the animal herein is a vertebrate, preferably a mammal, particularly a mammal except human and more preferably such an experimental animal as a rat, a rabbit, a guinea pig, a hamster, a dog and a cat and most preferably an ape such as a chimpanzee and a gorilla. The plant that can be applied by the method of the present invention is any plant classified into a seed plant and a sporic plant, an angiosperm and a gymnosperm, and a dicotyledon and a monocotyledon.

DESCRIPTION OF DRAWINGS

The application of the preferred embodiments of the present invention is best understood with reference to the accompanying drawings, wherein:

FIG. 1 is a photograph illustrating the thin layer chromatography examining products obtained from the culture of *Pseudomonas aeruginosa* PR3 using various natural vegetable oils as a substrate for 3 days.

FIG. 2 is a photograph illustrating the chemical structure of 7,10-dihydroxy-8(E)-octadecenoic acid produced from various substrates using *Pseudomonas aeruginosa* PR3.

FIG. 3 is a photograph illustrating the structure of 7,10-dihydroxy-8(E)-octadecenoic acid produced from various substrates using *Pseudomonas aeruginosa* PR3, confirmed by gas chromatograph/mass spectrometer.

FIG. 4 is a photograph illustrating the result of thin layer chromatography with the product indicated by arrow which was separated and purified among all the products produced on day 3 as shown in FIG. 1.

FIG. 5 is a photograph illustrating the antibacterial activity of 7,10-dihydroxy-8(E)-octadecenoic acid against *Salmonella typhimurium* KCTC 2515 and *Staphylococcus aureus* KCTC 1621 confirmed on a solid agar medium.

FIG. 6 is a photograph illustrating the dose-dependent inhibitory effect of 7,10-dihydroxy-8(E)-octadecenoic acid on the growth of a microorganism, *Bacillus subfillis* ATCC 6501 and *Ralstonia solanacearum* KACC 10475, in a liquid medium.

FIG. 7 is a table illustrating the antibacterial activity of 7,10-dihydroxy-8(E)-octadecenoic acid against various microorganisms confirmed on a solid agar medium.

FIG. 8 is a table illustrating the minimal inhibitory concentration of 7,10-dihydroxy-8(E)-octadecenoic acid for the antibacterial activity against various microorganisms confirmed by using a liquid medium.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Culture of *Pseudomonas aeruginosa* PR3 in the Presence of Natural Vegetable Oil <1-1> Culture of *Pseudomonas aeruginosa* PR3

*Pseudomonas aeruginosa* (Agricultural Research Service Culture Collection, USA; NRRL B-18602) was cultured in YPD medium (1% yeast extract, 2% peptone, 2% dextrose; pH 7.0) for 24 hours at 28° C., 200 rpm.

<1-2> Addition of Natural Vegetable Oil

Safflower seed oil, sesame oil, olive oil or grape seed oil was purchased on the market and added to the culture solution of Example <1-1> at the concentration of 1% individually or as a mixture, followed by additional incubation for 3 more days by the same manner as described in Example <1-1>. 6 N HCl was added to regulate the pH of the medium to 2.0 and the cultivation was terminated.

<1-3> Extraction of Culture Product

Upon completion of the culture, extraction was performed with ethyl acetate and diethyl ether whose amounts were respectively equal to the volume of the culture solution, stepwise, and then supernatant extracts were collected and concentrated in a rotary evaporator (Hanhn Shin Co, Korea).

EXAMPLE 2

Analysis with Thin Layer Chromatography

<2-1> Analysis of Culture Extract

The culture extract obtained in Example 1 and many different natural vegetable oils proceeded to thin layer chromatography
Lane 1: safflower seed oil;
Lane 2: microbial culture extract of safflower seed oil;
Lane 3: sesame oil;
Lane 4: microbial culture extract of sesame oil;
Lane 5: olive oil;
Lane 6: microbial culture extract of olive oil;
Lane 7: mixture of grape seed oil and olive oil (1:1); and,
Lane 8: microbial culture extract of mixture of grape seed oil and olive oil (1:1).

Particularly, 1 mg of the extract was loaded on the glass plate coated with silica gel, followed by separation of the compounds using the mixed solvent system comprising toluene:dioxane:acetic acid (79:14:7, v/v/v). After separation, 50% sulfuric acid solution was sprayed on the plate, followed by heating at 100° C. for at least 10 minutes. And then, appeared spots were confirmed.

As a result, as shown in FIG. 1, spots (arrows) indicating the difference between natural vegetable oil and the culture extract were confirmed.

<2-2> Analysis of Spots

Separation and purification of spots confirmed in Example <2-1> and the structure analysis were performed.

<2-2-1> Separation and Purification

The crude extract was expanded on thin layer chromatography by the same manner as described in Example <2-1>. The target compound was scrapped off from the plate. The target compound was recovered from silica gel using chloroform. The extraction was performed twice.

The isolates and the other products recovered from thin layer chromatography were analyzed by thin layer chromatography in the same manner as described in Example <2-1>.
Lane 1: triolein;
Lane 2: crude extract before purification;
Lane 3: product of separation & purification; and,
Lane 4: residual fraction after purification.

Figure 4:
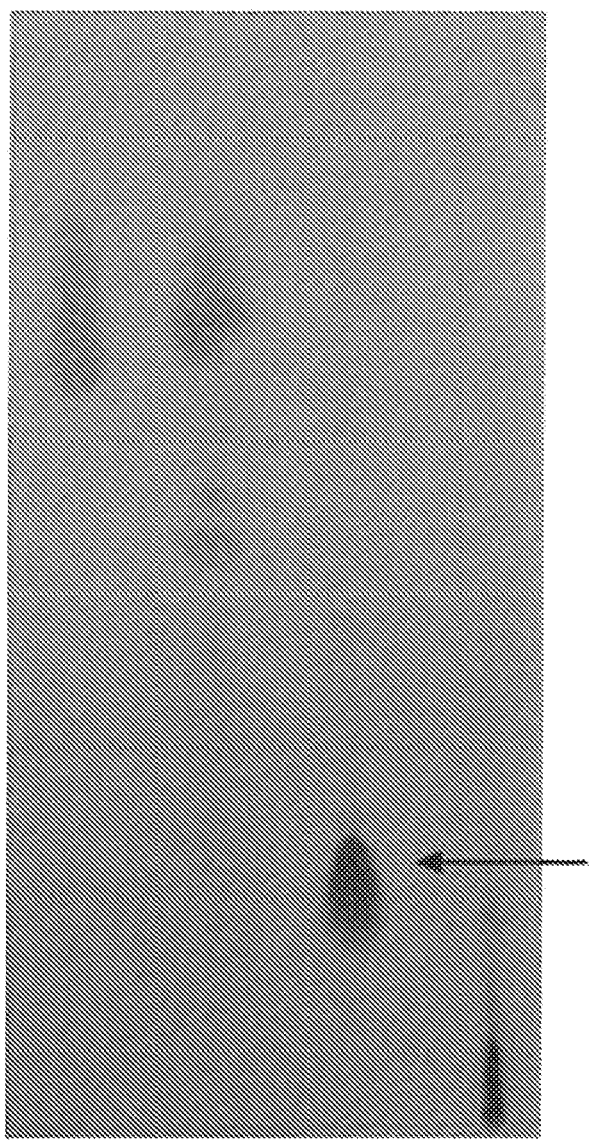

As a result, as shown in FIG. 4, a single spot (arrow) was detected in lane 3, suggesting that purification was successfully performed.

<2-2-2> Structure Analysis

The structure of the purified product obtained by the method of Example <2-2-1> was analyzed by gas chromatography/mass spectrometer.

Analysis with Gas Chromatography

One ml of diazomethane (diazald; Sigma Co, USA) in ether was added to 10 mg of the sample. After storage at room temperature for 5 minutes, Extra diazomethane and ether was eliminated by using nitrogen gas. 1 ml of TMSI+Pyridine (1:4, v/v) was added thereto, which stood for 40 minutes. The remaining solvent was eliminated by using nitrogen gas again, to which 200 µl of gas chromatography solution (Dichrolomethane:Methanol=95:5, v/v) was added. 1 µl of the final sample solution was injected to the gas chromatography (Shimadzu, Japan). At this time, a hydrophobic column (Supelco, USA) was used and the temperature was ranged between 100° C.-300° C. Time for the analysis was not more than 1 hour.

Analysis with Gas Chromatography/Mass Spectrometry

An analysis was performed in the same manner as described in the above gas chromatography. However, at this time, the column was at least 30 meter long (SPB-1, Supelco, USA) and the separated molecules were analyzed by mass spectrometry (Agilent, USA) equipped with the mass selective detector of the molecules.

As a result, as shown in FIG. 2 and FIG. 3, 7,10-dihydroxy-8(E)-octadecenoic acid (DOD) had the structure containing two hydroxyl groups, one being at C7 and the other being at C10 of C18 fatty acid chain, and one trans double bond between C8 and C9.

EXAMPLE 3

Antibacterial Activity of DOD

<3-1> Confirmation by Using a Solid Agar Medium 1

The antibacterial activity of DOD against *Salmonella typhimurium* KCTC 2515 and *Staphylococcus aureus* KCTC 1621 was investigated using a solid agar medium. The antibacterial activity can be investigated by measuring clear zone on the agar plate. The bigger the clear zone was, the higher the antibacterial activity was.
spot A: crude extract of the product bioconverted from triolein by a microorganism (3 mg);
spot B: Oleic acid (5 mg) (Sigma Co, USA);
spot C: Bactroban (3 mg Mupirocin) (Glaxo Smith Kline);
spot D: DOD (1 mg);
spot E: DOD (5 mg);
spot F: DMSO (20 µl) (Sigma Co, USA); and,
spot G: residue of the crude extract except DOD.

Particularly, 1.5% potato agar (Difco, USA) was added to YPD medium, and then the medium was sterilized. Twenty ml of the medium was distributed on a plastic Petri-dish and hardened to prepared a solid agar medium. KCTC2515 and KCTC 1621 were suspended in the YPD medium at the concentrations of $10^7$ cells/ml. Five hundred µl of the medium was inoculated on the solid agar medium. A sterilized filter paper (Whatman Co, USA) of 5 mm in diameter was placed on the solid agar medium, to which spot A-F materials were treated. DOD was diluted in DMSO (Sigma Co, USA) to a proper concentration and 20 µl of the diluent was treated thereto, followed by further culture for 2-3 days at 30° C. Then, the size of clear zone around the filter paper was measured to confirm the antibacterial activity.

Figure 5:
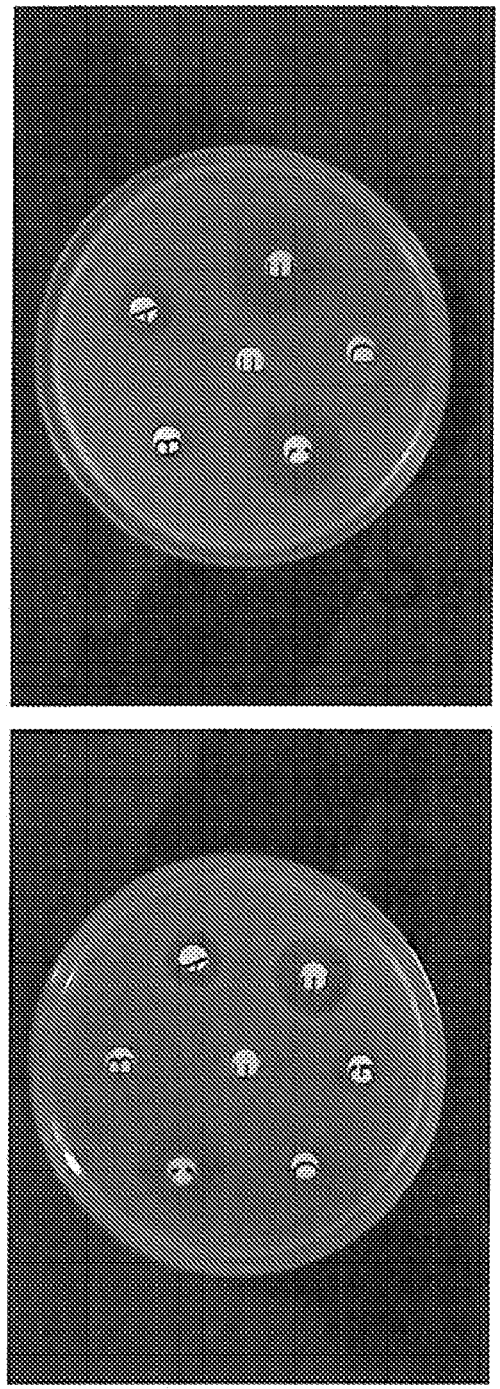

As a result, as shown in FIG. 5, DOD exhibited high antibacterial activity at the concentration of 5 mg/spot, which was similar level with that of Bactroban, a commercial antibacterial ointment.

<3-2> Confirmation by Using a Liquid Medium 1

The inhibitory effect of DOD on the growth of *Bacillus subtillis* ATCC 6501 and *Ralstonia solanacearum* KACC 10475 was investigated using a liquid medium.

Particularly, one ml of YPD medium was distributed in a 24-well plate. One hundred µl of DOD diluted to make final concentrations of 0.125 mg/ml-16 mg/ml was added to each well. *Bacillus subtillis* ATCC 6501 and *Ralstonia solanacearum* KACC 10475 were diluted in YPD medium, and 100 µl of which was inoculated into each well. The culture solution was recovered every 2 hours from the plate until 24 hours, from which cells were harvested by centrifugation followed by washing twice with distilled water. $OD_{540}$ was measured to investigate growth of the microorganisms. The amounts of the microorganisms were represented by a graph and the DOD concentration at which the microorganisms did not grow any more was determined as the minimal inhibitory concentration.

Figure 6:
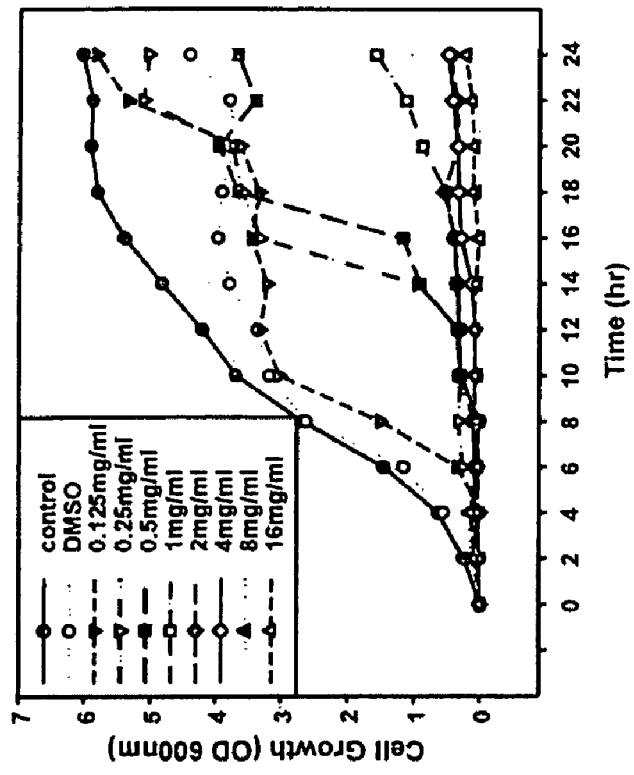
Figure 6:
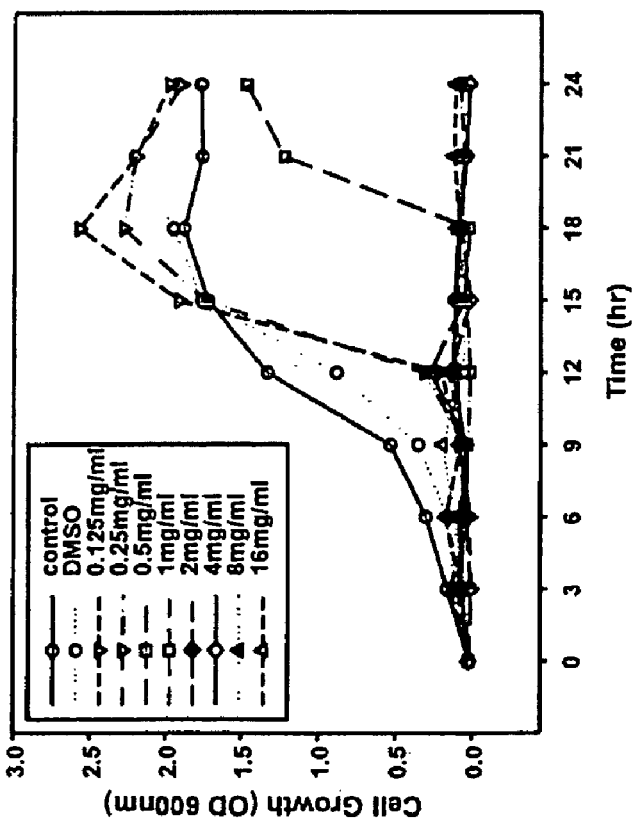

As a result, as shown in FIG. 6, the microorganisms did not grow at the certain concentration or up of DOD, suggesting that DOD had antibacterial activity to inhibit the growth of microorganisms in a liquid medium. The minimal inhibitory concentration for the microorganisms was <125 μg/ml, respectively (FIG. 8).

<3-3> Confirmation by Using a Solid Agar Medium 2

The inhibitory effect of DOD on the growth of *Escherichia coli* ATCC 8739(−), *Staphylococcus epidermidis* KCTC 1917(+), *Salmonella typhimurium* KCTC 2515(−), *Listeria monocytogenes* ATCC 19111(+), *Staphylococcus aureus* ATCC 6538(+) and *Bacillus subtilis* ATCC 6501(+) was investigated using a solid agar medium the same manner as described in Example <3-1> (−: Gram negative, +: Gram positive).

As a result, as shown in FIG. 7, DOD exhibited antibacterial activity against both Gram positive and Gram negative bacteria and therefore no specificity according to Gram staining was observed.

<3-4> Confirmation by Using a Liquid Medium 2

The antibacterial activity of DOD against various microorganisms was investigated using a liquid medium in the manner as described in Example <3-2>.

Particularly, the inhibitory effect of DOD on the growth of *Pseudomonas syringae* pv. *sesami* KACC 10649 (−), *Pseudomonas syringae* pv. *actinidae* KACC 10659 (−), *Erwinia* sp. KACC 10207 (−), *Pseudomonas syringae* pv. *syringae* KACC 10361 (−), *Ralstonia solanacearum* KACC 10475 (−), *Corynebacterium glutamicum* KACC 10784 (+), *Pseudomonas corrugate* KACC 10141 (−), *Xanthomonas axonopodis* pv. *citri* KACC 10443 (−), *Xanthomonas campestris* KACC 10490 (−) and *Clavibacter michiganesis* subsp. *Michiganensis* KACC 20122 (+) was investigated using a liquid medium by the same manner as described in Example <3-2> (−: Gram negative, +: Gram positive).

As a result, as shown in FIG. 8, DOD had growth inhibitory effect on various microorganisms except *Psuedomonas corrugate* KACC 10141 and *Clavibacter michiganesis* subsp. *Michiganensis* KACC 20122. And, no specificity according to Gram was observed.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating infective diseases caused by the pathogenic microorganisms in a subject comprising:
   administering 7,10-dihydroxy-8(E)-octadecenoic acid represented by <Formula 1> to the subject in an amount effective to inhibit the growth of the pathogenic microorganisms:

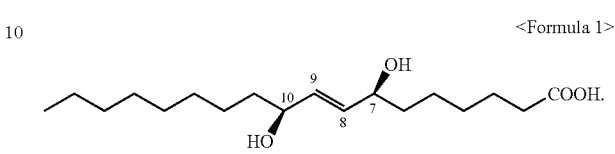

<Formula 1>

2. The method according to claim 1, wherein the pathogenic microorganisms are Gram positive or Gram negative bacteria.

3. The method according to claim 1, wherein the pathogenic microorganisms are selected from the group consisting of *Staphylococcus aureus, Bacillus subtillis, Escherichia coli, Staphylococcus epidermidis, Salmonella typhimurium, Listeria monocytogenes, Pseudomonas syringae pv. sesami, Pseudomonas syringae pv. actinidae, Erwinia sp., Pseudomonas syringae pv. syringae, Ralstonia solanacearum, Geotricum candidum, Rhizoctonia solani, Botrytis cinerea, Collectotrichum capsici, Fusarium oxysporum, Phytophtora capsici, Enterobacter agglomerans, Serratia marcescens, Yersinia pseudotuberculosis, Klebsiella pneumoniae, Arcanobacterium haemolyticum, Enterobacter intermedius, Agrobcaterium tumefaciens, Clavibacter michiganenesis, Erwinia chrysanthemi, Erwinia carotovora, Erwinia aroideae, Pseudomonas corrupta, Pseudomonas solanasearum, Pseudomonas gladioli, Xanthomonas campestris pv. citri, Xanthomonas campestri pv. prani, Botryosphaeria dothidea, Colletoricum gloesporiodes, Colletoricum acutuatum, Acidovora anthurii sp. Nov Agrobacterium sp., Malassezia furfur, Propionibacterium acnes, Trichophyton mentagrophytes, Trichophyton rubrum, Epidermophyton floccosum, Pseodumonas corrugate, Xanthomonas axonopodis pv. citri, Xanthomonas campestris, Cryptococcus neoformans, Candida albicans, Candida glabrata, Candida tropicalis, Rhodotorula rubra, Sacccharomyces cerevisiae, Trichosporon beigelii, Pichia memebranefaciens and Corynebacterium glutamicum.*

* * * * *